US006984382B1

(12) United States Patent
Groner et al.

(10) Patent No.: US 6,984,382 B1
(45) Date of Patent: Jan. 10, 2006

(54) BIFUNCTIONAL PROTEIN, PREPARATION AND USE

(75) Inventors: Bernd Groner, Lerchenstrasse 2, 4059 Basle (CH); Dirk Moritz, Basel (CH)

(73) Assignee: Bernd Groner, Basle/BS (CH)

( * ) Notice: Subject to any disclaimer, the term of this patent is extended or adjusted under 35 U.S.C. 154(b) by 746 days.

(21) Appl. No.: 09/596,774

(22) Filed: Jun. 19, 2000

Related U.S. Application Data

(63) Continuation of application No. 09/159,027, filed on Sep. 23, 1998, now abandoned, which is a continuation of application No. 08/793,048, filed as application No. PCT/EP95/01494 on Apr. 20, 1995, now abandoned.

(30) Foreign Application Priority Data

May 2, 1994 (EP) .................................. 94810244

(51) Int. Cl.
*A61K 35/12* (2006.01)
*A61K 35/14* (2006.01)
*C12N 5/10* (2006.01)

(52) U.S. Cl. .................. 424/93.71; 435/69.6; 435/69.7; 435/70.1; 435/328; 435/330; 435/344; 435/372.3; 435/69.1; 536/23.4; 536/23.53

(58) Field of Classification Search ............... 536/23.4, 536/23.53; 435/69.1, 320.1, 69.6, 69.7, 70.1, 435/328, 330, 344, 372.3; 424/93.71
See application file for complete search history.

(56) References Cited

U.S. PATENT DOCUMENTS 5,571,894 A  11/1996 Wels et al.
5,939,531 A   8/1999 Wels et al.

FOREIGN PATENT DOCUMENTS

| EP | 0260880 | 3/1988 |
|---|---|---|
| EP | 0336379 | 10/1989 |
| EP | 0499555 | 8/1992 |
| EP | 0 502 812 B1 | 9/1992 |
| EP | 0502812 | 9/1992 |
| EP | 0565794 | 10/1993 |
| WO | 8906692 | 7/1989 |
| WO | 9207943 | 5/1992 |
| WO | 9210591 | 6/1992 |
| WO | 9215322 | 9/1992 |
| WO | 9215326 | 9/1992 |
| WO | 9319163 | 9/1993 |
| WO | WO 95/30014 | 11/1995 |

OTHER PUBLICATIONS

Stancovski et al, "Targeting T Lymphocytes to Neu/Her2-expressing Cells Using Chimeric Single Chain Fv Receptors", The Journal of Immunology, 1993, vol. 151, pp. 6577-6582.*
Horgan et al, "Studies on the antigen binding by intact and hinge-deleted chimeric antibodies", Journal of Immunology, 1993, vol. 150, pp. 5400-5407. (abstract).*
Huse et al (Science, 1989, vol. 246, pp. 1275-1281).*
Verma et al (Nature, 1997, vol. 389, pp. 239-242).*
Eck et al (Gene-Based Therapy, In: The Pharmacological Basis of Therapeutics, Goodman and Gilman, Ed.s, 1996, pp. 77-101).*
Orkin et al ( "Report and Recommendation of the Panel to Assess the NIH Investment in Research on Gene Therapy", NIH, 1995).*
Clark (Protein Engineering of Antibody Molecules for Prophylactic and Therapeutic Applications in Man, 1993, p. 1).*
Abraham, et al., TIBS, vol. 17, 1992, pp. 434-438.
Baniyash, et al., J. Bio. Chem., vol. 263, No. 20, 1988, pp. 9874-9878.
Boon, Advances in Cancer Research, vol. 58, 1992, pp. 177-210.
Brocker, et al., Eur. J. Immunol., vol. 23, 1993, pp. 1435-1439.
Classon, et al., Int'l Immunol., vol. 4, 1992, No. 2, pp. 215-225.
Diamond, et al., J. Exp. Med., vol. 174, 1991, pp. 229-241.
Dohlsten, et al., PNAS (USA), vol. 88, 1991, pp. 9287-9291.
Eichmann, et al., J. Immunol., vol. 147, No. 7, 1991, pp. 2075-2081.
Eshhar, et al., J. Cell. Biochem., Suppl. 14B, 1990, pp. CE 112.
Eshhar, et al., PNAS (USA), vol. 90, 1993, pp. 720-724.
Frank, et al., Science, vol. 249, 1990, pp. 174-177.
Gross, et al., The FASEB Journal, vol. 6, 1992, pp. 3370-3378.
Hwu, et al., J. Exp. Med., vol. 178, 1993, pp. 361-366.

(Continued)

*Primary Examiner*—Karen A. Canella
(74) *Attorney, Agent, or Firm*—Heller Ehrman LLP

(57) ABSTRACT

A bifunctional protein comprising: 1) a single-chain antibody directed against a suitable antigen on a tumour cell, 2) a hinge region comprising from about 40 to about 200 amino acids joined to the $V_L$ domain of the single chain antibody, and 3) a functional zeta ($\zeta$) chain from the T-cell antigen receptor (TCR) joined to the hinge region, wherein the hinge region is an immunoglobin-like hinge region which is joined to the C-terminus of the $V_L$ domain of the single-chain antibody. The functional zeta ($\zeta$) chain comprises the transmembrane and the cytoplasmic domain. The bifunctional protein can be expressed using a cytotoxic lymphocyte (CTL) expressing DNA encoding it.

10 Claims, 1 Drawing Sheet

OTHER PUBLICATIONS

Hwu, et al., J. Immunol., vol. 150, No. 9, 1993, pp. 4104-4115.
Jin, et al., PNAS (USA), vol. 87, 1990, pp. 3319-3323.
Karasuyama, et al., Eur. J. Immunol., vol. 18, 1988, pp. 97-104.
Kast, et al., Cell, vol. 59, 1989, pp. 603-614.
Letourneur, et al., PNAS (USA), vol. 88, 1991, pp. 8905-8909.
Lopez, et al., Cytometry, vol. 10, 1989, pp. 165-173.
Miller, et al., Bio/Techniques, vol. 7, No. 9, 1989, pp. 980-986.
Morgenstern, et al., Nuc. Acids Res., vol. 18, No. 12, 1990, pp. 3587-3596.
Moritz, et al., Gene Therapy, vol. 2, 1995, pp. 539-546.
Moritz, et al., PNAS (USA), vol. 91, 1994, pp. 4318-4322.
Orloff, et al., Nature, vol. 347, 1990, pp. 189-191.
Orloff, et al., J. Bio. Chem., vol. 264, No. 25, 1989, pp. 14812-14817.
Riddell, et al., Science, vol. 257, 1992, pp. 238-240.
Romeo, et al., Cell, vol. 64, 1991, pp. 1037-1046.
Schlichtholz, et al., Cancer Research, vol. 52, 1992, pp. 6380-6384.
Shalaby, et al., J. Exp. Med., vol. 175, 1992, pp. 217-225.
Stancovski, et al., J. Immunol., vol. 151, 1993, pp. 6577-6582.
Weiss, Cell, vol. 73, Apr. 23, 1993, pp. 209-212.
Weissman, et al., PNAS (USA), vol. 85, 1988, pp. 9709-9713.
Weissman, et al., Science, vol. 239, 1988, pp. 1018-1021.
Wels, et al., Bio/Technology, vol. 10, 1992, pp. 1128-1132.
Winn, J. Immunol., vol. 86, No. 1, 1961, pp. 228-235.
Zamoyska, et al., Cell, vol. 43, 1985, pp. 153-163.
Meulenbroek, A.J. and Zeijlemaker, W.P., Human IgG Subclasses: Useful diagnostic markers for Immunocompetence (CLB 1996); <http://www.xs4all.nl/-ednieuw/IgGsubclasses/subkl23.htm>.

* cited by examiner

BIFUNCTIONAL PROTEIN, PREPARATION AND USE

CROSS REFERENCE TO RELATED APPLICATION

This application is a continuation of U.S. Ser. No. 09/159,027 filed Sep. 23, 1998, now abandoned, which is a continuation of U.S. Ser. No. 08/793,048 filed Nov. 1, 1996 now abandoned, from PCT National filing of PCT/EP95/01494 filed Apr. 20, 1995 under PCT Article 34 on Mar. 13, 1996, and which claims foreign priority benefits under 35 U.S.C. 119 of EPO 94810244.7 filed May 2, 1994.

The present invention relates to a bifunctional protein capable of directing a host cell producing said protein to specifically recognize selected target cells. Furthermore, the invention provides a method for the preparation of said protein, a DNA construct encoding said protein, a composition comprising a host cell expressing said DNA, and antibodies specifically recognizing said protein. Additionally, the invention relates to the use of such a host cell, e.g. for selectively killing tumor cells in vitro or in vivo.

The principle of adoptive immunotherapy, also referred to as cellular immunotherapy, is the transfer of immunologically active cells to a mammal in order to enhance the mammal's immune response to a disease state. To this end the immune cells are removed e.g. from the human patient or another subject, cultured, optionally in the presence of immunoenhancing agents such as interleukin 2, and subsequently (re-)administered to the patient, conventionally in the presence of an immunoenhancing agent. In the patient, the immunologically active cells act to alleviate the disease state.

Immunologically active cells suggested for adoptive immunotherapy include lymphokine activated killer (LAK) cells, derived from natural killer (NK) cells, and in vitro sensitized lymphocytes (IVS), derived from cytolytic or cytotoxic T lymphocytes (CTL), also referred to as killer T lymphocytes. LAK cells are cytolytic cells which react with a broad spectrum of target cells. They are not major histocompatibility complex (MHC)-restricted and capable of lysing tumor cells, but also normal cells in vitro. CTL have clonal specificities, i.e. each clone is specific for a particular antigenic structure on the surface of a target cell. A particular CTL recognizes and binds a unique antigen and thus becomes activated and can then multiply and destroy the target cells. The recognition process is MHC-restricted and dependent, since an antigen is recognized only in association with one of the self class I MHC surface molecules expressed by the target cell.

Recognition of a specific antigen by T cells is mediated by the T-cell antigen receptor (TCR) (A. Weiss, Cell 73, 209–212 (1993)). Binding of a ligand to the receptor may trigger cellular effector programs, such as activation of tyrosine kinases, intracellular calcium ion release and interleukin 2 production (R. T. Abraham et al., Trends Biochem. Sci. 17, 434–438 (1992)).

The TCR is a multimeric surface complex comprising the products of at least six genes, all of which are required for efficient plasma membrane expression. The clonotypic alpha (α) and beta (β) chains of the TCR mediate specific target cell recognition. These chains are non-covalently associated with the non-polymorphic components of the CD3 complex gamma (γ), delta (δ), and epsilon (ε), and the zeta (ζ) chain. The disulfid-linked ζ homodimer is a transmembrane molecule and its cytoplasmic part plays a central role in the TCR-mediated signal transduction and induction of cytolysis. The ζ chain is capable of autonomous signal transduction, i.e. ζ alone is sufficient to mediate a response. Fusion of the ζ chain with an extracellular ligand binding domain may result in a molecule which can be activated by interaction with the ligand (S. J. Frank et al., Science 249, 174–177 (1990); C. Romeo & B. Seed, Cell 64, 1037–1046 (1990); F. Letourneur & R. D. Klausner, Proc. Natl. Acad. Sci. USA 88, 8905–8909 (1991)). An isoform of ζ, eta (η), represents an alternatively spliced form of the ζ gene transcript.

Tumor formation involves the mutation of oncogenes and tumor suppressor genes in somatic cells. Such mutations may result in structural alterations or in the overexpression of proteins. Both events might lead to alterations in the intracellular processing of these proteins and the presentation of new antigenic structures in association with the major histocompatibility antigens on the surface of the cells. The detection of antibodies directed against oncogene products in the serum of tumor patients is an indication that oncogene products can be antigenic. Further evidence for this antigenicity is the evocation of the cellular immune response. The occurrence of CTL which recognize and eliminate tumor cells has been demonstrated in a number of model systems (T. Boon, Adv. Cancer Res. 58, 177–210 (1992); M. W. Kast et al., Cell 59, 603–614 (1989); Disis et al., Cancer Res. 54, 16–20 (1994)).

Present strategies aimed at exploiting the cytolytic activity of T-lymphocytes, e.g. for the treatment of cancer, suffer from several shortcomings, such as MHC-restriction of the recognition process in naturally occurring CTL. There is a need for an approach to overcome the limitations currently encountered.

It is the object of the present invention to provide such an improved approach involving manipulation of CTL-recognition specificity, e.g. to make the altered CTL potent and selective anti-tumor agents. This approach is based on the identification of consistent genetic alterations in benign and particularly in malignant tumor cells. Providing CTL with a defined tumor cell specificity enables the targeting to defined tumor cells and MHC-unrestricted and MHC-independent destruction of said target cells. Tumor cell lysis by CTL grafted with a novel, MHC independent recognition specificity may be exploited in vitro (ex vivo) or in vivo, e.g. in a gene therapy approach involving cancer treatment.

The tumor cells are (pre-)defined or selected target cells in that they carry the antigenic structure (ligand) recognized and bound by the antigen binding domain which is part of the chimeric protein of the invention.

The present invention concerns a chimeric protein capable of directing a CTL to specifically recognize and kill selected tumor cells. More specifically, the present invention provides a chimeric protein comprising a recognition function, a hinge region and the ζ chain of the TCR, and a CTL producing one or more of such protein molecules. Binding of a cell-bound ligand to the recognition part of the chimeric protein of the invention leads to ζ chain-mediated signal transduction within the CTL and eventually results in the lysis of the cell carrying the ligand.

The chimeric protein of the invention is a protein which does not exist in nature. The protein is bifunctional in that it is capable of both specifically recognizing and binding to a particular antigenic structure (via its recognition function domain) and serving as a signalling component (via the ζ chain part). The hinge region serves as a spacer and ensures the necessary accessibility and flexibility of the recognition function domain. The hinge region is understood to be essential for the functionality of the chimeric protein of the invention. Preferably, the arrangement within the chimeric protein is such that the recognition function is located at the N-terminus and linked to the ζ chain part at the C-terminus of the chimeric protein via the hinge region. Being a cell surface receptor molecule the chimeric protein of the invention comprises an extracellular domain, a transmembrane domain and a cytoplasmic domain and is inserted into the plasma membrane of the host cell, e.g. the CTL. The functionality of the protein of the invention within the host cell is detectable in an assay suitable for demonstrating the signalling potential of said protein upon binding of a particular ligand, e.g. in an assay enabling detection of a signalling pathway triggerred upon binding of the ligand, such as an assay involving measurement of the increase of calcium ion release, intracellular tyrosine phosphorylation, inositol phosphate turnover or interleukin (IL) 2, interferon γ, GM-CSF, IL-3, IL-4 production thus effected. (R. T. Abraham et al., Trend Biochem. Sci. 17, 434–438 (1992)). Such assays are readily available to the person with ordinary skill in the art. Reference is made to the assays employed in the Examples. It is evident that these assays may be modified, e.g. by using other suitable cell lines.

The recognition function is contributed by an antigen binding domain of an antibody, particularly a single chain antibody (scFv). Single chain antibodies are gene fusions comprising the variable domains of the heavy and light chain of monoclonal antibodies. Said recognition and binding function is conferred to the ζ-chain of the TCR-complex to circumvent MHC-restricted antigen recognition through the α/β chains of the TCR.

The antigen binding domain is derivable from a monoclonal antibody directed against and specific for a suitable antigen on a tumor cell.

A suitable antigen is an antigen with enhanced or specific expression on the surface of a tumor cell as compared to a normal cell, e.g. an antigen evolving from consistent genetic alterations in tumor cells. Examples of suitable antigens include ductal-epithelial mucine, gp 36, TAG-72, growth factor receptors and glycosphingolipids and other carbohydrate antigens preferentially expressed in tumor cells (Please give references for the below captioned antigens and antibodies). Ductal-epithelial mucine is enhancedly expressed on breast, ovarian and pancreas carcinoma cells and is recognized e.g. by monoclonal antibody SM3 (Zotter et al., Cancer Rev. 11, 55–101 (1988)). The glycoprotein gp 36 is found on the surface of human leukemia and lymphoma cells. An exemplary antibody recognizing said antigen is SN 10. TAG-72 is a pancarcinoma antigen recognized by monoclonal antibody CC49 (Longenecker, Sem. Cancer Biol. 2, 355–356). Growth factor receptors are e.g. the human epidermal growth factor (EGF) receptor (Khazaie et al., Cancer and Metastasis Rev. 12, 255–274 (1993)) and HER2, also referred to as erbB-2 or gp 185 (A. Ullrich and J. Schlessinger, Cell 61, 203–212 (1990)). The erbB-2 receptor is a transmembrane molecule which is overexpressed in a high percentage of human carcinomas (N. E. Hynes, Sem. in Cancer Biol. 4, 19–26 (1993)). Expression of erbB-2 in normal adult tissue is low. This difference in expression identifies the erbB-2 receptor as "tumor enhanced".

Preferably, the antigen binding domain is obtainable from a monoclonal antibody produced by using as immunogen viable human tumor cells presenting the antigen in its native form. In a preferred embodiment of the invention, the recognition part of the chimeric protein specifically binds to an antigenic determinant on the extracellular domain of a growth factor receptor, particularly HER 2. Monoclonal antibodies directed to the HER2 growth factor receptor are known and are described, for example, by S. J. Mc Kenzie et al., Oncogene 4, 543–548 (1990), R. M. Hudziak et al., Molecular and Cellular Biology 9, 1165–1172 (1989), International Patent Application WO 89/06692 (Genentech) and Japanese Patent Application Kokai 02–150 293 (Ajinomoto K K). Monoclonal antibodies raised against viable human tumor cells presenting HER2 in its native form, such as SKBR3 cells, are described, for example, in European patent application EP-A-502 812 (Ciba-Geigy) which is enclosed herein by reference, and include antibodies FRP5, FSP16, FSP77 and FWP51. Hybridoma cell lines producing these antibodies have been deposited with the European Collection of Animal Cell Cultures (ECACC, PHLS Centre for Applied Microbiology & Research, Porton Down, Salisbury, UK) on Nov. 21, 1990 under accession numbers 90112115, 90112116, 90112117 and 90112118, respectively.

In the chimeric protein of the invention, the preferred antigen binding domain is a single-chain recombinant antibody (scFv) comprising the light chain variable domain ($V_L$) bridged to the heavy chain variable domain ($V_H$) via a flexible linker (spacer), preferably a peptide. Advantageously, the peptide consists of about 10 to about 30 amino acids, particularly naturally occurring amino acids, e.g., about 15 naturally occurring amino acids. Preferred is a peptide consisting of amino acids selected from L-glycine and L-serine, in particular the 15 amino acid peptide consisting of three repetitive units of Gly—Gly—Gly—Gly-Ser (residues 1–5 of SEQ ID NO: 12). Advantageous is a single chain-antibody wherein $V_H$ is located at the N-terminus of the recombinant antibody. Preferred is a chimeric protein wherein the single-chain recombinant antibody has an above-defined preferred specificity, e.g., a chimeric protein comprising a single-chain recombinant antibody wherein the heavy chain variable domain and the light chain variable domain are derivable from a monoclonal antibody, e.g., a murine monoclonal antibody, directed to the human growth factor receptor HER2, such as a murine monoclonal antibody selected from the group consisting of FSP16, FSP77, FRP5 and FWP51.

The variable domain of an antibody heavy or light chain consists of so-called framework regions (FRs), which are fairly conserved in antibodies with different specificities, and of hypervariable regions also called complementarity determining regions (CDRs), which are typical for a particular specificity. In the antigen binding domain of a chimeric protein according to the invention, preferably the FRs are derivable from a mammalian, e.g. a murine or particularly a human antibody. The scFv derivative of a monoclonal antibody is grafted onto the ζ chain of the TCR/CD3 complex.

Particularly preferred is a chimeric protein comprising a single-chain recombinant antibody wherein the heavy chain variable domain comprises a polypeptide of the formula

$$FR_1—CDR_{1H}—FR_2—CDR_{2H}—FR_3—CDR_{3H}—FR_4 \qquad (I)$$

wherein the polypeptide chain is described as starting at the N-terminal extremity and ending at the C-terminal extremity and $FR_1$ is a peptide residue comprising at least 25–29, preferably 25–33 naturally occurring amino acids, $FR_2$ is a peptide residue comprising 12–16 naturally occurring amino acids, $FR_3$ is a peptide residue comprising 30–34 naturally occurring amino acids, $FR_4$ is a peptide residue comprising at least 6–10, preferably 6–13 naturally occurring amino acids, $CDR_{1H}$ is a peptide residue of the amino acid sequence 31 to 35 of SEQ ID NO:2, $CDR_{2H}$ is a peptide residue of the amino acid sequence 50 to 66 of SEQ ID NO:2, and CDR$_{3H}$ is a peptide residue of the amino acid sequence 99 to 108 of SEQ ID NO:2, or, CDR$_{1H}$ is a peptide residue of the amino acid sequence 31 to 35 of SEQ ID NO:4, CDR$_{2H}$ is a peptide residue of the amino acid sequence 50 to 66 of SEQ ID NO:4, and CDR$_{3H}$ is a peptide residue of the amino acid sequence 99 to 109 of SEQ ID NO:4, and wherein the amino acid Cys may be in the oxidized state forming S—S-bridges. These particular complementarity determining regions are Asn-Tyr-Gly-Met-Asn (CDR$_{1H}$), Trp-Ile-Asn-Thr-Ser-Thr-Gly-Glu-Ser-Thr-Phe-Ala-Asp—Asp-Phe-Lys-Gly (CDR$_{1H}$), and Trp-Glu-Val-Tyr-His-Gly-Tyr-Val-Pro-Tyr (CDR$_{3H}$) according to SEQ ID NO:2, or Ser-Tyr-Trp-Met-Asn (CDR$_{1H}$), Met-Ile-Asp-Pro-Ser-Asp-Ser-Glu-Thr-Gln-Tyr-Asn-Gln-Met-Phe-Lys-Asp (CDR$_{2H}$) and Gly—Gly-Ala-Ser-Gly-Asp-Trp-Tyr-Phe-Asp-Val (CDR$_3$H) according to SEQ. ID NO:4.

Especially preferred is a chimeric protein wherein the recombinant single-chain antibody comprises a heavy chain variable domain of formula I, wherein the framework regions FR$_1$, FR$_2$, FR$_3$ and FR$_4$ are those preferably derivable from a mammalian, especially a murine or a human antibody.

In a first embodiment of the invention, most preferred is a chimeric protein wherein the heavy chain variable domain of the recombinant single-chain antibody comprises a polypeptide of the amino acid sequence 2 to 120, of SEQ ID NO:2, wherein optionally one or more, e.g. 1, 2, 3 or 4, single amino acids within the amino acid sequences 2 to 30 (FR$_1$), 36 to 49 (FR$_2$), 67 to 98 (FR$_3$), and/or 110 to 120 (FR$_4$), are replaced by other amino aids or deleted, and wherein the amino acid Cys may be in the oxidized state forming S—S-bridges, in particular a chimeric protein wherein the heavy chain variable domain comprises a polypeptide of the amino acid sequence 6 to 119 of SEQ ID NO:2, wherein the amino acid Cys may be in the oxidized state forming S—S-bridges.

In a second embodiment of the invention, most preferred is a chimeric protein wherein the heavy chain variable domain of the recombinant single-chain antibody comprises a polypeptide of the amino acid sequence 2 to 120 of SEQ ID NO:4; wherein optionally one or more, e.g. 1, 2, 3 or 4, amino acids within the amino acid sequences 2 to 30 (FR$_1$), 36 to 49 (FR$_2$), 67 to 98 (FR$_3$), and/or 110 to 120 (FR$_4$), are replaced with other amino acids or deleted, and wherein the amino acid Cys may be in the oxidized state forming S—S-bridges, in particular the recombinant antibodies with a heavy chain variable domain comprising a polypeptide of the amino acid sequence 6 to 120 of SEQ ID NO:4, wherein the amino acid Cys may be in the oxidized state forming S—S-bridges.

For example, a hydrophobic amino acid within a framework region may be replaced by another amino acid, preferably also a hydrophobic amino acid, e.g. a homologous amino acid, replaced with two amino acids (resulting in the insertion of an amino acid), or deleted. Likewise, a hydrophilic amino acid within a framework region may be replaced with another amino acid, two amino acids or deleted, whereby replacing amino acids preferably maintain the hydrogen bond structure of the corresponding framework region. Advantageously, any replacement of one or more amino acids takes into account the guidelines known in the art for reshaping or humanizing of an antibody. Particularly noteworthy are guidelines aimed at reducing the immunogenicity of the reshaped antibody (as compared to the "original" monoclonal antibody) and/or at designing an antibody which about equals or exceeds the binding affinity of the "original" antibody. A modification of amino acids may be confined to a single FR, i.e. FR$_1$, FR$_2$, FR$_3$ or FR$_4$, or involve two, three or all four of the FRs.

A likewise preferred chimeric protein of the invention comprises a recombinant single-chain antibody wherein the light chain variable domain comprises a polypeptide of the formula

$$FR_6—CDR_{1L}—FR_7—CDR_{2L}—FR_8—CDR_{3L}—FR_9 \qquad (II)$$

wherein the polypeptide chain is described as starting at the N-terminal extremity and ending at the C-terminal extremity and FR$_6$ is a peptide residue comprising naturally occurring amino acids, preferably 19–25, especially 19–23 naturally occurring amino acids, FR$_7$ is a peptide residue comprising 13–17 naturally occurring amino acids, FR$_8$ is a peptide residue comprising 30–34 naturally occurring amino acids, FR$_9$ is a peptide residue comprising naturally occurring amino acids, particularly 7–11 naturally occurring amino acids, and CDR$_{1L}$ is a peptide residue of the amino acid sequence 158 to 168 of SEQ ID NO:2, CDR$_{2L}$ is a peptide residue of the amino acid sequence 184 to 190 of SEQ ID NO:2, and CDR$_{3L}$ is a peptide residue of the amino acid sequence 223 to 231 of SEQ ID NO:2, or CDR$_{1L}$ is a peptide residue of the amino acid sequence 159 to 164 of SEQ ID NO:4, CDR$_{2L}$ is a peptide residue of the amino acid sequence 185 to 191 of SEQ ID NO:4, and CDR$_{3L}$ is a peptide residue of the amino acid sequence 224 to 231 of SEQ ID NO:4, and wherein the amino acid Cys may be in the oxidized state forming S—S-bridges. These particular complementarity determining regions are Lys-Ala-Ser-Gln-Asp-Val-Tyr-Asn-Ala-Val-Ala (CDR$_{1L}$), Ser-Ala-Ser—Ser-Arg-Tyr-Thr (CDR$_{2L}$), and Gln—Gln-His-Phe-Arg-Thr-Pro-Phe-Thr (CDR$_{3L}$) according to SEQ ID NO:2, or Lys-Ala-Ser-Gln-Asp-Ile-Lys—Lys-Tyr-Ile-Ala (CDR$_{1L}$), Tyr-Thr-Ser-Val-Leu-Gln-Pro (CDR$_{2L}$) and Leu-His-Tyr-Asp-Tyr-Leu-Tyr-Thr (CDR$_{3L}$) according to SEQ ID NO:4.

Especially preferred is a chimeric protein wherein the recombinant antibody comprises a light chain variable domain of formula II, wherein the peptide residues of the framework regions FR$_5$, FR$_6$, FR$_7$ and FR$_8$ are those derivable from a mammalian, especially a murine or a human, antibody.

In one embodiment of the invention, most preferred is a chimeric protein wherein the recombinant antibody comprises a light chain variable domain comprising a polypeptide of the amino acid sequence 135 to 240 of SEQ ID NO:2, wherein optionally one or more, e.g. 1, 2, 3 or 4, amino acids within the amino acid sequences 135 to 157 (FR$_6$), 169 to 183 (FR$_7$), 191 to 222 (FR$_8$), and/or 232 to 240 (FR$_9$) are replaced by other amino acids or deleted, and wherein the amino acid Cys may be in the oxidized state forming S—S-bridges, in particular a light chain variable domain comprising a polypeptide of the amino acid sequence 135 to 240 of SEQ ID NO:2, wherein the amino acid Cys may be in the oxidized state forming S—S-bridges.

In a second embodiment of the invention, most preferred is a chimeric protein wherein the recombinant antibody comprises a light chain variable domain comprising a polypeptide of the amino acid sequence 136 to 240 of SEQ ID NO:4, wherein optionally one or more, e.g. 1, 2, 3 or 4 single amino acids within the amino acid sequences 136 to 158 (FR$_6$), 170 to 184 (FR$_7$), 192 to 223 (FR$_8$), and/or 232 to 240 (FR$_9$) are replaced by other amino acids or deleted, and wherein the amino acid Cys may be in the oxidized state forming S—S-bridges, in particular a light chain variable domain comprising a polypeptide of the amino acid sequence 136 to 240 of SEQ ID NO:4, wherein the amino acid Cys may be in the oxidized state forming S—S-bridges.

For example, amino acids within the framework regions may be replaced by other amino acids or deleted as detailed above for the heavy chain.

Especially preferred is a chimeric protein comprising a single-chain recombinant antibody wherein the heavy chain variable domain and the light chain variable domain are linked by way of a spacer group consisting of 10 to 30, e.g. about 15, amino acids, in particular a single-chain recombinant antibody comprising a polypeptide of the formula

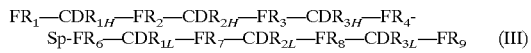

wherein the polypeptide chain is described as starting at the N-terminal extremity and ending at the C-terminal extremity and $FR_1$, $CDR_{1H}$, $FR_2$, $CDR_2H$, $FR_3$, $CDR_{3H}$, $FR_4$, $FR_6$, $CDR_{1L}$, $FR_7$, $CDR_{2L}$, $FR_8$, $CDR_{3L}$ and $FR_9$ have the meanings as mentioned before and Sp is a peptide spacer as disclosed above.

The antigen binding domain may be tested for its specificity to a predefined tumor cell antigen by methods known in the art, for example by immunofluorescent staining of cells expressing high levels of the antigen, by immunoblotting either directly or by way of immunoprecipitation and protein blotting of the immunocomplexes, or by another immunoassay such as binding, crossinhibition or competition radio- or enzyme immunoassay. The binding affinity of the antigen binding domain may be determined using a suitable quantitative assay which can easily be established by a person with ordinary skill in the art based on known techniques and principles. If desired, the affinity of the antigen binding domain may be compared to the affinity of a suitable reference antibody, e.g. the "parental" monoclonal mouse antibody it is derivable from.

Additionally to the antigen binding domain the chimeric protein of the invention comprises a hinge region which is inserted as a short, flexible tether between the antigen binding domain and the ζ domain. The hinge region is a peptide comprising from about 40 to about 200 naturally occurring amino acids, preferably from about 60 to about 190 amino acids. Preferably, the hinge region in the chimeric protein according to the invention is an immunoglobulin-like hinge region, e.g. a hinge region derivable from the CD4 molecule, such as the D3D4 immunoglobulin domains (P. J. Maddon et al., Proc. Natl. Acad. Sci. USA. 84, 9155–9159 (1987)) or a hinge region derivable from the CD8α molecule, e.g. Lyt-2 (R. Zomoyska et al., Cell 43, 153–163 (1985); B. J. Classon et al., Int. Immunol. 4, 2, 215–225 (1992)). In the amino acid sequence set forth in SEQ ID No. 7 the hinge region (Lyt-2) extends from the amino acid at position 245 to the amino acid at position 304.

Additionally to the antigen binding domain and the hinge region the chimeric protein of the invention comprises a functional ζ domain contributing the transmembrane and the signalling domain of the chimeric protein. A functional ζ domain essentially comprises the transmembrane and the cytoplasmic domain of the ζ chain. The ζ domain mediated activation of the TCR by interaction of the antigen binding domain of the chimeric protein of the invention with a specific antigen triggers several signalling pathways, e.g. the ones mentioned above. According to the invention the ζ chain is of mammalian, particularly murine or, human origin. Within the TCR ζ exists a ζζ disulphide homodimer. A functional ζ domain is a protein which upon expression in T cell hybridomas deficient in endogenous ζ expression is capable of restoring in said hybridomas a functionally active TCR, e.g. in such a way that antigen-induced interleukin-2 secretion and growth stimulation are regained (S. Frank et al., Science 249, 174–177 (1990)). Examples of a functional ζ domain include molecules comprising amino acids 28 to 164 of the murine (A. M. Weissman, Science 239, 1018–1021 (1988)) and amino acids 28 to 163 of the human ζ chain (numbering according to A. M. Weissmann et al., Proc. Natl. Acad. Sci. USA 85, 9709–9713 (1988), FIG. 2, which is incorporated herein by reference). It is envisaged that a ζ protein as used for the purpose of the present invention is intended to include variants with the provision that these variants are functional. Preferred are variants of mammalian, particularly murine and human origin.

For example, a variant is a naturally occurring variant of the ζ molecule as found within a particular species. Such a variant may be encoded by a related gene of the same gene family or an allelic variant of a particular gene. The term "variant" also embraces a modified ζ molecule producible from a DNA which has been subjected to in vitro mutagenesis, with the provision that the protein encoded by the DNA has the functional activity of the authentic ζ molecule. Such modifications may consist in an addition, exchange and/or deletion of one or more amino acids, the latter resulting in shortened variants.

A preferred chimeric protein of the invention comprises a protein having the amino acid sequence depicted in SEQ ID No. 7.

Moreover, the invention relates to a polyclonal and monoclonal antibody specifically binding to a protein of the invention. Such an antibody is prepared according to conventional methods well known in the art.

The chimeric protein of the invention may be prepared by a process that is known per se, characterized in that suitable host cells as defined further below producing a protein of the invention, are multiplied in vitro or in vivo, and, if desired, the protein is isolated. Preferably, a protein of the invention is produced by a process comprising culturing suitable transduced CTL under conditions which allow the expression of the DNA construct encoding the protein and, optionally, performing an assay detecting the functionality of the protein. The invention further concerns a method for the manufacture of a chimeric protein of the invention comprising culturing a suitable host cell, particularly a CTL, which has been transduced with a vector comprising an expression cassette comprising a promoter and a DNA coding for said protein which DNA is controlled by said promoter under conditions which allow the expression of said DNA. A preferred chimeric protein of the invention is constructed to include a scFv, a hinge region and a functional ζ molecule. The process for producing the chimeric protein of the invention should yield the protein in an amount sufficient to enable the transduced host cell to lyse a target cell.

Suitable host cells include e.g. primary cytotoxic T lymphocytes (CD 8+), CD 4+ T helper cells and natural killer cells (NK). Preferred are mammalian cells, especially CTL of mammalian, particularly human origin.

As used hereinbefore or hereinafter, in vitro means ex vivo, thus including cell culture conditions.

For example, multiplication of mammalian cells in vitro is carried out in suitable culture media, which are customary standard culture media, such as Dulbecco's Modified Eagle Medium (DMEM) or RPMI 1640 medium, optionally replenished by a mammalian serum, e.g. fetal calf serum, or trace elements and growth sustaining supplements, e.g. feeder cells.

The invention also concerns a recombinant DNA or DNA construct suitable for manipulating the recognition specificity of T-lymphocytes. More specifically, the present invention provides a DNA construct capable of directing the synthesis of a chimeric protein comprising a recognition function, a hinge region and the ζ-chain as a signalling component of the TCR. In particular, the invention provides a DNA construct encoding a chimeric protein comprising an antigen binding domain, a hinge region and a ζ domain, particularly a DNA construct comprising at least one polynucleotide coding for a protein part designated as preferred hereinbefore or hereinbelow. In a preferred arrangement the antigen binding domain is conceived as the first part, the hinge region as the second part and the ζ chain as the third part.

By definition the DNAs of the invention include coding single stranded DNAs, double stranded DNAs consisting of said coding DNAs and DNA complementary thereto, or these complementary (single stranded) DNAs themselves.

Advantageously, the DNA construct of the invention comprises a fourth part which is located upstream of the first part (the antigen binding domain) and which encodes a leader peptide. Preferably, the fourth part of the DNA construct of the invention encodes a leader peptide of an immunoglobulin (Ig) gene, e.g. an Ig heavy chain leader peptide. The Ig heavy chain leader peptide promotes targeting of nascent polypeptides to the lumen of the endoplasmic reticulum; it is subsequently cleaved off and the protein is sorted through the Golgi and the membrane to its transmembrane location. Particularly preferred is a leader peptide having the sequence: Met-Ala-Trp-Val-Trp-Thr-Leu—Leu-Phe-Leu-Met-Ala—Ala—Ala-Lys-Val-.Pro-Lys (residues 1–18 of SEQ ID NO: 6).

Preferred is a DNA comprising a DNA encoding the protein with the amino acid sequence depicted in SEQ ID No.7, e.g. a DNA having the nucleotide sequence depicted in SEQ ID No. 5. The DNA sequence set forth in SEQ ID No. 7 has the following features: description of the sequence: 5'-EcoRI-IgH chain leader D6/12-scFv(FRP5):Lyt-2 hinge:CD3 zeta(transmembrane (TM) and cytoplasmic (Cyt))-EcoRI-3'

| | |
|---|---|
| 5'EcoRI site: | position 1 |
| 3'RcoRI site: | position 1474 |
| ATG initiation | position 40 |
| TAA stop | position 1423 |
| IGH chain leader | position 40–93 |
| scFv(FRP5) | position 94–819 |
| lyt-2 hinge insert | XbaI (position 819)–XbaI (position 1005) |
| zeta insert | XbaI (position 1005)–EcoRI (position 1474) |

The present state of the art is such that a person with ordinary skill in the art will be able to synthesize a DNA molecule of the invention given the written information provided herein. A suitable method for obtaining a DNA construct of the invention involves methods well-known in the art comprising e.g. synthesis of a number of oligonucleotides, amplification of specific gene sequences, e.g. using PCR (polymerase chain reaction) technology, their splicing to give the desired DNA sequence and/or use of DNA restriction enzymes and ligases. A DNA of the invention may be synthesized by combining chemical with recombinant methods.

The invention further concerns a vector, such as a retroviral vector, comprising a DNA construct of the invention.

Additionally, the present invention provides a genetically engineered transduced CTL which is capable of destroying a targeted tumor cell in an MHC-independent and MHC-unrestricted manner. According to the present invention, the CTL produces the above-identified chimeric protein of the invention. The CTL is transduced with a DNA of the invention and thus is capable of expressing said DNA and of producing the protein encoded by said DNA. Destruction of the targeted tumor cell requires that the protein thus produced is functional, i.e. the antigen binding domain of said protein must be capable of recognizing and binding to the targeted tumor cell and the ζ domain must be capable of triggering the desired signal within the CTL. The CTL of the invention is cultured under conditions enabling (favoring) the expression of the introduced DNA and, if desired, assayed for the production thereof. Prolonged and elevated expression of said DNA is preferred.

Furthermore, the present invention provides a process for endowing a CTL with a defined, MHC-independent and MHC-unrestricted tumor cell specificity by introducing into said T-lymphocyte a DNA construct comprising a recognition function, a spacer domain and the ζ-chain as a signalling component of the TCR. The DNA construct may be introduced into the CTL by DNA-transfer methods apparent to those skilled in the art, e.g. by means of a vector system, such as a viral or non-viral vector system. Suitable viral vectors include retroviral, adenoviral and adeno-associated viral vectors. The process is applicable to both in vivo and in vitro situations. In vitro application is preferred.

The T-lymphocyte is cultured under conventional conditions allowing the expression of said DNA construct and assayed for the production thereof. Prolonged and elevated expression of said DNA is preferred. Advantageously, CTL are cultured in the presence of IL-2. Transduced CTL of the invention may be selected for a suitable marker. For example, the transduced CTL may be selected for the cotransduced neo resistance marker if the DNA construct of the invention is transferred via a retroviral vector.

Moreover, the invention relates to a composition of matter comprising the transduced CTL of the invention. Such a composition comprises e.g. transduced CTL producing a protein of the invention together or in admixture with an acceptable, e.g. a pharmaceutically acceptable, carrier. Such a carrier may be a solid or liquid carrier. The composition may be used ex vivo, e.g. in order to kill preselected target cells in a composition (for example body liquid or tissue) removed from a patient's body. After the target cells have been killed (which should be checked) the composition is re-introduced into the patient's body. Thus the composition of the invention may be used for the treatment or adjuvant treatment of tumors.

Additionally, the present invention provides a process for lysing selected tumor cells comprising contacting said tumor cells to CTL producing the chimeric protein of the invention. In the process which is applicable to both in vitro and in vivo situations the tumor cell is targeted by the antigen binding domain which is part of the chimeric protein of the invention.

It is preferred to use the host's own CTL, particularly if the exposure and interaction is to occur in vivo, but, if appropriate, the CTL may also be derived from other sources. Other sources are e.g. tissue culture or another mammal of the same or different species.

CTL are found throughout the body of the mammal: in tissues, the lymphatic system and in the blood. Suitable CTL are selected and removed from the mammal. For example, CTL are selected as CD8+ peripheral lymphocytes cultured in vitro in the presence of IL-2. Alternatively, unselected peripheral lymphocytes are used for gene transduction. If desired, the host may be treated such as to increase the number of stimulated CTL.

The invention further concerns a method of treating cancer comprising the use of the genetically engineered CTL of the invention. The method comprises exposing selected tumor cells to CTL producing the chimeric protein of the invention. An in vitro (meaning ex vivo) application of this method for promotion of CTL-mediated lysis may be in the selective treatment of tumor cells removed from a mammal, particularly a human, in the need of cancer treatment. An example would be to use the CTL of the invention to eliminate tumor cells from bone marrow removed from a patient, e.g. a patient undergoing radiation treatment prior, to re-introducing the bone marrow. As a consequence of the interaction of the tumor cells and the CTL of the invention the tumor cells are lysed. If the method of treating cancer is performed in vivo it may further comprise re-introducing the transduced CTL of the invention into the body of the mammal, particularly the human, to be treated. It is also envisaged that CTL expressing a DNA of the invention are produced by in vivo transduction of the DNA, e.g. in a mammal in need of cancer treatment.

The invention further concerns the CTL of the invention or a composition comprising said CTL for use in a method of treating cancer.

The invention particularly concerns the specific embodiments (e.g. protein, DNA, CTL and methods for the preparation thereof) described in the Examples. The following examples illustrate the invention but do not limit it to any extent.

Abbreviations: FCS: fetal calf serum; LDH: lactate dehydrogenase; mAb: monoclonal antibody; MoMLV: Moloney murine leukemia virus; MoMLV-LTR: Moloney murine leukemia virus-long terminal repeat, scFv: single chain antibody; SDS-PAGE: sodium dodecylsulfate polyacrylamide gel electrophoresis.

Materials and Methods

Cell Lines and Culture Conditions

Clone 96 (C196) is a H-2 $K^d$-restricted cytotoxic T cell line derived from C57BL/6 mice (K. Eichmann et al., J. Immunol. 147, 2075–2081 (1991)). C196 and infectants are maintained in Dulbecco's modified Eagle's medium (DMEM, Gibco) supplemented with 10% FCS (Boehringer), $5 \times 10^{-5}$ M 2-mercaptoethanol, 10 mM HEPES, 2 mM L-glutamine and 3% conditioned supernatant obtained from X63Ag8-653 plastocytoma cells transfected with the murine Il-2 cDNA (H. Karasuyama and F. Melchers, Eur. J. Immunol. 18, 97–104 (1988)). The human leukemic T cell line Jurkat, the retroviral packaging cell lines ΩE (J. P. Morgenstern and H. Land, Nuc. Acids Res. 18, 3587–3596 (1990)) and P317 (A. D. Miller and G. J. Rosman, Biotechniques 7, 980–990 (1989)) and infectants and the murine fibroblast cell line transfected with the activated human erbB-2 receptor, NIH3T3#3.7 are cultured in DMEM supplemented with 10% FCS. HC11R1#11 is a mouse mammary epithelial cell line transfected with the human erbB-2 proto-oncogene (N. E. Hynes et al., Mol. Cell. Biol. 10, 4027–4034 (1990)) which is grown in RPMI 1640 (Gibco) supplemented with 10% FCS, 10 ng/ml epidermal growth factor and 5 µg/ml insulin.

EXAMPLE 1

Construction of the scFv(FRP5):hinge:zeta(ζ) cDNA

A DNA consisting of a recognition function, a spacer domain and the ζ-chain as a signalling component of the TCR/CD3 receptor complex is constructed. The recognition function is contributed by a scFv domain. This domain is derived from the monoclonal antibody FRP5 (European patent application EP-A-502 812). FRP5 is specific for the extracellular domain of the erbB-2 receptor. The scFv (FRP5) comprises the variable domains of the heavy and light chains ($V_H$ and $V_L$) of the monoclonal antibody (mAb) joined by a 15 amino acid linker sequence (SEQ ID NO:2). This scFv domain is able to recognize the extracellular domain of the erbB-2 receptor (W. Wels et al., Biotechnology 10, 1128–1132 (1992); W. Wels et al., Cancer Res. 15, 6310–6317 (1992)). A leader sequence from an immunoglobulin heavy chain is added to the N-terminus of the scFv domain. The scFv(FRP5) cDNA is ligated to a short linker sequence encoding 59 amino acids from the immunoglobulin-like hinge region of the CD8α gene (R. Zomoyska et al., Cell 43, 153–163 (1985)). The transmembrane and signalling domain are contributed by the ζ-chain of the TCR. This chain is responsible for the signal transduction following TCR activation.

The cDNA encoding the single chain antibody FRP5 specific for the extracellular domain of the erbB-2 molecule (SEQ ID NO:1) is subcloned into a plasmid containing an immunoglobulin heavy chain leader ($L_{IgH}$). Both, the ζ cDNA and the CD8α hinge cDNA are derived from total RNA of the cytotoxic T cell line C196 using a combination of reverse transcription and the polymerase chain reaction (RT-PCR). MoMLV reverse transcriptase is used for first strand cDNA synthesis. The reactions are primed with the 3' ζ-specific oligonucleotide 5813 (SEQ ID NO:6) or the 3' CD8α-specific oligonucleotide 8764 (SEQ ID NO:7), respectively. These cDNAs are used as PCR templates with the ζ primer pair 5812/5813 (SEQ ID NOs. 8 and 6) introducing a 5' XbaI site and a 3' HindIII/BglII site and the CD8α hinge primer pair 8763/8764 (SEQ ID NOs. 10 and 8) introducing a XbaI site at both ends. The $L_{IgH}$-scFv (FRP5) DNA is ligated to the ζ cDNA starting from amino acid residue 28 (numbering according to A. M. Weissman et al., Science 239, 1018–1021 (1988)) using the XbaI site for the fusion. The CD8α hinge cDNA encoding amino acid residues 105 to 164 (numbering according to R. Zomoyska et al., Cell 43, 153–163 (1985)) is subsequently inserted into the XbaI site and checked for right orientation. The resulting scFv:hinge:ζ cDNA construct (SEQ ID No. 7) is confirmed by complete DNA sequencing and eventually subcloned into the unique EcoRI site of the pLXSN retroviral vector (A. D. Miller and G. J. Rosman, supra) resulting in the pL(scFv (FRP5):hinge:ζ) SN construct. The expression of the DNA is controlled by the 5' MoMLV-LTR. The plasmid also bears a selectable marker for neomycin resistance driven by the SV40 early promoter (SN).

Cloning of pL(scFv:D3/D4:ζ)SN

While the first molecular design includes the relatively short and flexible immunoglobulin hinge-like region of the murine Lyt-2 or CD8α molecule as tether, the second design encompasses the two membrane-proximal immunoglobulin-like domains designated as D3 and D4 of the murine L3T4 or CD4 molecule (S. J. Clark et al., Proc. Natl. Acad. Sci. USA 84, 1649–1653 (1987)) as a longer and more rigid spacer. D3/D4 encoding cDNA is obtained by PCR using pcd-L3T4 4.25 plasmid DNA (D. R. Littman and S. N. Gettner, Nature 325, 453–455 (1987)). The specific primer pair #8761/#8762 amplifies the coding sequences for amino acid residues 184–370 of the CD4 molecule (P. J. Maddon et al., Proc. Natl. Acad. Sci. USA 84, 9155–9159 (1987)) introducing XBaI restriction sites at both ends of the cDNA. The product is subcloned into the XbaI site of the pL(FZ)SN vector. After checking for the correct orientation of the insert, sequence identity of the resulting construct is confirmed by DNA sequencing. The structure of the pL(F4Z)SN is shown in FIG. 1.

Primers for the amplification of the L3T4/CD4D3/D4cDNA:

'Upstream'-5'Lyt-2/CD8-specific oligonucleotide #8761[1]):
8761: 5'-AGCTTCTAGAGTTTCAGAGCA-CAGCTCTCACGGCC-3' (SEQ ID NO: 13)

'Downstream'-3'Lyt-2/CD8-specific oligonucleotide #8762[1]): #8762: 5'-TCGATCTAGAGTCTGGTTCAC-CCCTCTGG-3' (SEQ ID NO: 14).

EXAMPLE 2

Expression of the scFv(FRP5):hinge:ζ DNA after Retroviral Gene Transfer

The pLXSN vector system is capable of directing the efficient synthesis of the scFv(FRP5):hinge:ζ DNA after transduction into cytotoxic T cells and allows for G418 selection of infected cells. An established murine CTL line, C196, is infected with the pL(scFv(FRP5):hinge:ζ)SN construct of Example 1.

The ecotropic packaging cell line ΩE is transfected by calcium-phosphate precipitation with pL(scFv(FRP5):hinge:ζ)SN plasmid DNA. Transfected cells are stably selected in the presence of the neomycin analogue G418 (Geniticin, 1 mg/ml, Gibco). Viral supernatants are harvested after 48 hours from pools of G418 resistant helper cells and used to infect the amphotropic packaging cell line PA317 in the presence of 8 mg/ml polybrene. Clonal, high titer producer lines are derived by selection in 1.0 mg/ml G418 containing medium. Supernatants of these producer lines are used to infect C196 cells. Clones of infected cells selected for high expression of the scFv(FRP5):hinge:ζ DNA are derived and assayed for the production of chimeric cell surface proteins (Example 3). Clone CFYZ.1 is derived by growth in 1.0 mg/ml G418. Jurkat cells are infected using the same procedure, the clone JFYZ.4 is derived by growth in 2.0 mg/ml G418.

EXAMPLE 3

Biochemical Characterization of Cell Surface Proteins a) SDS-PAGE analysis of the chimeric scF(FRP5):hinge:ζ proteins produced by transduced CTL Selected clones of Example 2 are cell surface biotinylated, lysed and immunoprecipitated with an anti-ζ mAb. For surface biotinylation, $3 \times 10^7$ viable cells are washed three times in biwa buffer (PBS, 1 mM $MgCl_2$, 0.1 mM $CaCl_2$) and resuspended in 1.5 ml Sulfo-NHS Biotin in biwa buffer (Pierce, 0.5 mg/ml). After incubating 15 min at 4° C., the reaction is quenched by addition of 25 mM L-lysine in biwa buffer. The cells are washed three times in quenching buffer (25 mM L-lysine in biwa buffer) and lysed in 1% NP-40, 150 mM NaCl, 50 mM Tris/HCL pH 8.0, 5 mM EDTA, 1 mM PMSF containing buffer supplemented with a protease inhibitor cocktail. Postnuclear lysates are precleared overnight with Protein A Sepharose (Pharmacia). Immunoprecipitation is performed by addition of 3 mg of the ζ-specific mAb H146-968 which recognizes human and mouse COOH-terminus of the ζ chain, incubated for 3 hours followed by 1 hour incubation with Protein A Sepharose. The preciptitate is washed four times in NET-TON (650 mM NaCl, 5 mM EDTA, 50 mM Tris/HCl, 0.5% Triton X-100, 1 mg/ml ovalbumin). For deglycosylation, precipitates are denatured in 5% SDS with or without 10% 2-mercaptoethanol at 100° C. and incubated with 2.000 U PNGase F (Biolabs) for 1 hour at 37° C. Samples are boiled in either non-reducing or reducing Laemmli-sample buffer and electrophoresed through 5–20% SDS-PAGE gradient gels. The proteins are transferred to a PVDF membrane (Millipore) and blocked in PBS-T (PBS, 0.4% Tween-20) containing 5% skim milk powder (Fluka). The membrane is incubated for one hour with PBS-T containing horseradish peroxidase-streptavidin (HRP-Strep, Southern Biotechnology, 1:5.000). After washing the membrane four times for 7 min in PBS-T, the blot is developed using the ECL-chemoluminescence reagent (Amersham). The SDS-PAGE analysis of the immunoprecipitates under reducing conditions reveals a series of bands with an apparent molecular weight of about 48–65 kDa from lysates of infected cells (clone CFYZ.1), but not in lysates of the parental cells (C196 cells). The 48 kDa band corresponds to the scFv(FRP5):hinge:ζ protein with a calculated molecular weight of 48.7 kDa. The amino acid sequence of said protein is depicted in SEQ ID NO:5. In said sequence listing the recognition part derived from mAb FRP5 extends from the amino acid at position 6 (Gln) to the amino acid at position 240 (Ile), the hinge region derived from CD8α extends from the amino acid at position 245 (Ile) to the amino acid at position 304 (Phe) and the ζ chain extends from the amino acid at position 307 (Asp) to the amino acid at position 443 (Arg). The higher molecular weight species arise as a consequence of complex glycosylation of the scFv and the hinge region. Deglycosylation with the endoglycosidase PNGase F results in a simplified protein pattern and the reduction of the apparent molecular weight to about 47 kDa. The endogenous ζ-chain is detected as a 16 kDa band (16.3 kDa predicted) in uninfected and infected cells. When the SDS-PAGE analysis is carried out under non-reducing conditions, both disulfide-linked scFv:hinge:ζ homodimers with an apparent molecular weight of about 96 kDa as well as heterodimers of scFv(FRP5):hinge:ζ molecules with the endogenous ζ with an apparent molecular weight of about 64 kDa are observed. PNGase F treatment slightly reduced the molecular weights of these two bands. The detected 32 kDa band corresponds to endogenous ζ-ζ homodimers of the CTL.

b) Flow Cytometric Analysis of scFv(FRP5):hinge:ζ Protein Producing T Cells

Cell surface expression and erbB-2 receptor binding ability of the scFv(FRP5):hinge:ζ protein in transduced C196 CTL and in transduced Jurkat cells are confirmed by flow cytometry.

Single-cell suspensions of $5 \times 10^5$ viable cells (Jurkat cells, JFYZ.4 cells, C196 cells, CFYZ.1 cells) are stained with the purified extracellular domain of the erbB-2 protein (erbB-$2^{ecd}$, expressed in Sf9 insect cells using a baculovirus expression vector; Disis et al., Cancer Res. 54, 16–20 (1994)) for 1 hour followed by the FITC-conjugated anti-erbB-2 monoclonal antibody FSP77 (European patent application EP-A-502 812) for 45 min at 4° C. in 100 µl PBS containing 1% BSA and 0.1% sodium azide. FSP77 also is specific for the extracellular domain of the erbB-2 receptor, but recognizes a different epitope from mAb FRP5 (I. M. Harwerth et al., J. Biol. Chem. 21, 15160–15167 (1992)). Ten thousand forward scatter/side scatter gated viable cells are acquired and analysed with a flow cytometer revealing binding of the purified, soluble extracellular domain of the erbB-2 receptor to the transduced T cells JFYZ.4 and CFYZ.1 but not to non-infected Jurkat or C196 cells.

The hinge region provides flexibility and accessibility to the scFv moiety and is a necessary prerequisite for the binding of the extracellular domain of the erbB-2 receptor to the scFv domain. Insertion of the CD4 D3D4 also allows binding. A construct in which a direct fusion, without a hinge region or spacer, of the scFv domain to the ζ-chain is tested, results in a surface receptor which cannot bind to the erbB-2 protein.

EXAMPLE 4

Signal Transduction of the scFv(FRP5):hinge:ζ Fusion Protein

The intracellular calcium ($Ca^{2+}$) concentration of T cells loaded with a suitable calcium-chelating fluorescent dye is measured after incubation with the soluble erbB-2 receptor. For this purpose cultured JFYZ.4 infectants and Jurkat cells are suspended at $1 \times 10^7$/ml in RPMI 1640 supplemented with 2% FCS and 5 mM Indo-1/AM (Calbiochem) (M. Lopez et al., Cytometry 10, 165–173 (1989)) and rotated for 45 min at 37° C. After washing twice, $3 \times 10^5$ cells are incubated on ice with 2 mg purified erbB-$2^{ecd}$. Triggering is performed at 37° C. by simultaneous administration of 5 mg anti-erbB-2 mAb FSP77 followed by crosslinking with a goat anti-mouse Ig antiserum (GαM Ig, Southern Biotechnology). As a control, cells are triggered by addition of anti-human CD3ε mAb (Serva) and GαM Ig. Calcium flux is monitored for 15 min on a flow cytometer by measuring emission at 405 and 525 nm.

Crosslinking results in a rapid increase of intracellular calcium in JFCZ.4 cells but not in parental Jurkat cells comparable to that obtained by crosslinking the CD3 complex with an anti-CD3ε mAb in non-infected cells. This indicates that intracellular signalling is triggerred upon crosslinking of the scFv(FRP5):hinge:ζ protein via an extracellular ligand domain and that the scFv(FRP5):hinge:ζ protein is functionally active.

EXAMPLE 5

In Vitro Cytotoxicity Assay

The cytolytic activity of infected C196 (CFYZ.1) cells is determined in vitro. Oncogenically transformed mouse NIH3T3 fibroblasts and HCl 1 epithelial cells expressing the human erbB-2 receptor (N. E. Hynes et al., supra)) are employed as target cells. The release of LDH from these cells is used as a measure of cell lysis (T. Decker and M. L. Lohmann-Matthes, J. Immunol. Methods 115, 61–69 (1988)). The cytotoxicity assay is performed in phenol red free medium supplied with 4% conditioned supernatant containing recombinant murine Il-2 (rmIl-2, see above). A constant number of target cells (7.500/well) is added to a serial 2-fold dilution of effectors (CFYZ.1 cells) followed by an eight hour incubation at 37° C. and 5% $CO_2$. All dilutions are performed in triplicates. The LDH content of a 50 µl aliqout of the supernatant is assayed using the CytoTox 96 assay (Promega) (T. Decker and M. L. Lohmann-Matthes, supra). The LDH activity measured after lysis of target cells with 0.4% Triton X-100 is considered as 100%. The measured experimental values are corrected for the spontaneous release of LDH from effector and target cells. Infected C196 cells expressing the scFv(FRP5):hinge:ζ construct efficiently lyse erbB-2 expressing NIH3T3 cells or HC11 cells at effector to target ratios between 1 and 10. Lysis of the epithelial and fibroblast target cells ttransfected with the human erbB-2 receptor occurs in a non MHC-restricted manner indistinguishable from normal antigen-specific cellular cytotoxicity. In contrast, no cell lysis is observed when the parental C196 cells are used as effectors. The mAb FRP5 and the derived scFv domain are specific for the human erbB-2 molecule and do not recognize the mouse homologue which is expressed at low levels on both cell lines. For this reason, no cell lysis is observed when untransfected NIH/3T3 cells or HC11 cells are incubated with the scFv(FRP5):hinge:ζ construct expressing T cells.

EXAMPLE 6

In Vivo Anti-Tumor Activity

Two experimental schedules are used to assess the antitumor activity of the transduced CTL (infected C196 cells) in vivo. In the first schedule, $5 \times 10^5$ NIH3T3#3.7 tumor cells are mixed with $5 \times 10^6$ CFYZ.1 cells or parental C196 cells (effector to target ratio of 1:10) in 0.1 ml culture medium and immediately injected subcutaneously (s.c.) into the right flank of Balb/c nude mice (H. J. Winn, J. Immunol. 86, 228–234 (1961)). The growth of the tumors is followed by caliper measurements. NIH3T3#3.7 tumor cells alone are injected as a control. Each group consists of five animals. In the second schedule, Balb/c nude mice are inoculated s.c. into the right flank with $4 \times 10^5$ NIH3T3#3.7 tumor cells. On day 4 and 5, when tumors are palpable, parental C196 cells and CFYZ.1 cells are injected intravenously into the tail vein ($1 \times 10^7$ cells in 0.2 ml culture medium). 500 U of rhIl-2 (Hoffmann-La Roche) in 0.2 ml PBS are administered intraperitoneally on days 4, 5 and 6. The growth of the tumors is followed by caliper measurements. NIH3T3#3.7 cells without Il-2 and with Il-2 are injected as controls. Each group consists of five animals. NIH/3T3 cells transformed with the human erbB-2 oncogene lead to the rapid formation of tumors after subcutaneous injection into athymic Balb/c nude mice. The simultanous administration of CFYZ.1 infectants and tumor cells completely suppresses tumor formation for up to 7 days. Administration of the uninfected parental C196 cells, however has no effect on tumor cell growth. A similar result is obtained when nude mice are inoculated first with NIH3T3-erbB-2 tumor cells and subsequently treated with CFYZ.1 cells in combination with exogenous Il-2. The administration of the transduced CTL strongly retards the growth of the tumor cells over a course of seven days thus showing a systemic in vivo effect. The cells have the capability to home the tumor, to be activated and display their cytolytic activity when administered at a different site.

These results show that the specificity and thus the cytolytic effector machinery of the transduced CTL can be efficiently redirected towards a predefined surface antigen, the erbB-2 receptor, which plays an important role in the etiology of many human adenocarcinomas including breast, ovarian, gastric and colon cancer. Therefore the principle of targeted T cell action is conceived as a useful therapy approach and generally applicable for the elimination of tumor cells which express a surface antigen at higher levels than normal cells. The design permits the generation of CTL with many desired specificities by exchanging the scFv moiety and replacing it with any existing antigen recognition function derived from a specific monoclonal antibody. The use of efficient transfer systems, e.g. retroviral vectors, allows the transfer of scFv:hinge:ζ DNAs into cell types which are not easily transfectable.

Deposition Data:

Hybridoma cell lines producing antibodies FRP5, FSP16, FSP77 and FWP51 have been deposited with the European Collection of Animal Cell Cultures (ECACC, PHLS Centre for Applied Microbiology & Research, Porton Down, Salisbury, UK) on Nov. 21, 1990 tinder accession numbers 90112115, 90112116, 90112117 and 90112118, respectively.

SEQUENCE LISTING

Figure 1:
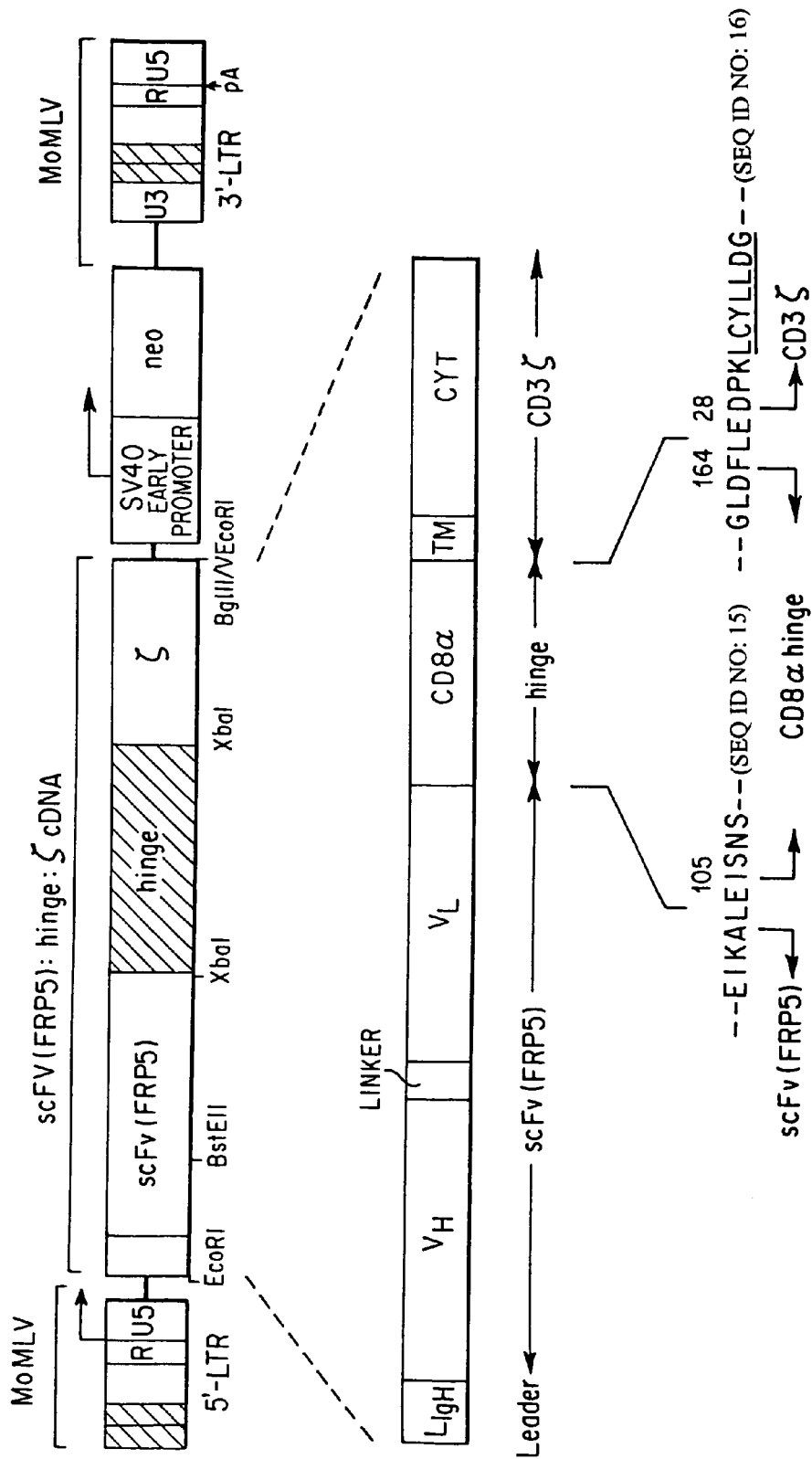
FIG. 1: Structure of the pL(F4Z)SN retroviral vector. A cDNA encoding amino acid residues number 184–370 of the CD 4 immunoglobulin like D3 and D4 domains is derived by PCR and subcloned into the XbaI site of the PL(FX)SN vector. Amino acid sequences of the fusion boundaries are shown in the single letter code (SEQ ID NOS 15 and 16).

```
<160> NUMBER OF SEQ ID NOS: 16

<210> SEQ ID NO 1
<211> LENGTH: 748
<212> TYPE: DNA
<213> ORGANISM: Artificial Sequence
<220> FEATURE:
<223> OTHER INFORMATION: Description of Artificial Sequence: Synthetic
      chimeric nucleotide sequence
<220> FEATURE:
<221> NAME/KEY: CDS
<222> LOCATION: (9)..(728)

<400> SEQUENCE: 1 aagcttct cag gta caa ctg cag cag tct gga cct gaa ctg aag aag cct        50
         Gln Val Gln Leu Gln Gln Ser Gly Pro Glu Leu Lys Lys Pro
           1               5                      10 gga gag aca gtc aag atc tcc tgc aag gcc tct ggg tat cct ttc aca        98
Gly Glu Thr Val Lys Ile Ser Cys Lys Ala Ser Gly Tyr Pro Phe Thr
 15                  20                  25                  30 aac tat gga atg aac tgg gtg aag cag gct cca gga cag ggt tta aag       146
Asn Tyr Gly Met Asn Trp Val Lys Gln Ala Pro Gly Gln Gly Leu Lys
                 35                  40                  45 tgg atg ggc tgg att aac act tcc act gga gag tca aca ttt gct gat       194
Trp Met Gly Trp Ile Asn Thr Ser Thr Gly Glu Ser Thr Phe Ala Asp
             50                  55                  60 gac ttc aag gga cgg ttt gac ttc tct ttg gaa acc tct gcc aac act       242
Asp Phe Lys Gly Arg Phe Asp Phe Ser Leu Glu Thr Ser Ala Asn Thr
 65                  70                  75 gcc tat ttg cag atc aac aac ctc aaa agt gaa gac atg gct aca tat       290
Ala Tyr Leu Gln Ile Asn Asn Leu Lys Ser Glu Asp Met Ala Thr Tyr
 80                  85                  90 ttc tgt gca aga tgg gag gtt tac cac ggc tac gtt cct tac tgg ggc       338
Phe Cys Ala Arg Trp Glu Val Tyr His Gly Tyr Val Pro Tyr Trp Gly
 95                 100                 105                 110 caa ggg acc acg gtc acc gtt tcc tct ggc ggt ggc ggt tct ggt ggc       386
Gln Gly Thr Thr Val Thr Val Ser Ser Gly Gly Gly Gly Ser Gly Gly
                115                 120                 125 ggt ggc tcc ggc ggt ggc ggt tct gac atc cag ctg acc cag tct cac       434
Gly Gly Ser Gly Gly Gly Gly Ser Asp Ile Gln Leu Thr Gln Ser His
            130                 135                 140 aaa ttc ctg tcc act tca gta gga gac agg gtc agc atc acc tgc aag       482
Lys Phe Leu Ser Thr Ser Val Gly Asp Arg Val Ser Ile Thr Cys Lys
                145                 150                 155 gcc agt cag gat gtg tat aat gct gtt gcc tgg tat caa cag aaa cca       530
Ala Ser Gln Asp Val Tyr Asn Ala Val Ala Trp Tyr Gln Gln Lys Pro
            160                 165                 170
```

```
gga caa tct cct aaa ctt ctg att tac tcg gca tcc tcc cgg tac act     578
Gly Gln Ser Pro Lys Leu Leu Ile Tyr Ser Ala Ser Ser Arg Tyr Thr
175                 180                 185                 190 gga gtc cct tct cgc ttc act ggc agt ggc tct ggg ccg gat ttc act     626
Gly Val Pro Ser Arg Phe Thr Gly Ser Gly Ser Gly Pro Asp Phe Thr
                195                 200                 205 ttc acc atc agc agt gtg cag gct gaa gac ctg gca gtt tat ttc tgt     674
Phe Thr Ile Ser Ser Val Gln Ala Glu Asp Leu Ala Val Tyr Phe Cys
            210                 215                 220 cag caa cat ttt cgt act cca ttc acg ttc ggc tcg ggg aca aaa ttg     722
Gln Gln His Phe Arg Thr Pro Phe Thr Phe Gly Ser Gly Thr Lys Leu
        225                 230                 235 gag atc tagctgatca aagctctaga                                        748
Glu Ile
    240

<210> SEQ ID NO 2
<211> LENGTH: 240
<212> TYPE: PRT
<213> ORGANISM: Artificial Sequence
<220> FEATURE:
<223> OTHER INFORMATION: Description of Artificial Sequence: Synthetic
      chimeric amino acid sequence

<400> SEQUENCE: 2

Gln Val Gln Leu Gln Gln Ser Gly Pro Glu Leu Lys Lys Pro Gly Glu
1               5                   10                  15

Thr Val Lys Ile Ser Cys Lys Ala Ser Gly Tyr Pro Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Ser Thr Gly Glu Ser Thr Phe Ala Asp Asp Phe
    50                  55                  60

Lys Gly Arg Phe Asp Phe Ser Leu Glu Thr Ser Ala Asn Thr Ala Tyr
65                  70                  75                  80

Leu Gln Ile Asn Asn Leu Lys Ser Glu Asp Met Ala Thr Tyr Phe Cys
                85                  90                  95

Ala Arg Trp Glu Val Tyr His Gly Tyr Val Pro Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Asp Ile Gln Leu Thr Gln Ser His Lys Phe
    130                 135                 140

Leu Ser Thr Ser Val Gly Asp Arg Val Ser Ile Thr Cys Lys Ala Ser
145                 150                 155                 160

Gln Asp Val Tyr Asn Ala Val Ala Trp Tyr Gln Gln Lys Pro Gly Gln
                165                 170                 175

Ser Pro Lys Leu Leu Ile Tyr Ser Ala Ser Ser Arg Tyr Thr Gly Val
            180                 185                 190

Pro Ser Arg Phe Thr Gly Ser Gly Ser Gly Pro Asp Phe Thr Phe Thr
        195                 200                 205

Ile Ser Ser Val Gln Ala Glu Asp Leu Ala Val Tyr Phe Cys Gln Gln
    210                 215                 220

His Phe Arg Thr Pro Phe Thr Phe Gly Ser Gly Thr Lys Leu Glu Ile
225                 230                 235                 240

<210> SEQ ID NO 3
```

<210> SEQ ID NO 3
<211> LENGTH: 748
<212> TYPE: DNA
<213> ORGANISM: Artificial Sequence
<220> FEATURE:
<223> OTHER INFORMATION: Description of Artificial Sequence: Synthetic chimeric nucleotide sequence
<220> FEATURE:
<221> NAME/KEY: CDS
<222> LOCATION: (9)..(728)

<400> SEQUENCE: 3

```
aagcttct cag gta caa ctg cag cag tct ggg gct gag ctg gtg agg cct      50
         Gln Val Gln Leu Gln Gln Ser Gly Ala Glu Leu Val Arg Pro
          1               5                  10 ggg act tca gtg aag ctg tcc tgc aag gct tct gat tac acc ttc acc       98
Gly Thr Ser Val Lys Leu Ser Cys Lys Ala Ser Asp Tyr Thr Phe Thr
 15                  20                  25                  30 agc tac tgg atg aac tgg gtg aag cag agg cct gga caa ggc ctt gaa      146
Ser Tyr Trp Met Asn Trp Val Lys Gln Arg Pro Gly Gln Gly Leu Glu
                     35                  40                  45 tgg att ggt atg att gat cct tca gac agt gaa act caa tac aat caa      194
Trp Ile Gly Met Ile Asp Pro Ser Asp Ser Glu Thr Gln Tyr Asn Gln
 50                  55                  60 atg ttc aag gac aag gcc gca ttg act gta gac aag tcc tcc aat aca      242
Met Phe Lys Asp Lys Ala Ala Leu Thr Val Asp Lys Ser Ser Asn Thr
             65                  70                  75 gcc tac atg caa ctc agc agc ctg aca tct gag gac tct gcg gtc tat      290
Ala Tyr Met Gln Leu Ser Ser Leu Thr Ser Glu Asp Ser Ala Val Tyr
 80                  85                  90 tac tgt gca aaa ggg ggg gcc tct ggg gac tgg tac ttc gat gtc tgg      338
Tyr Cys Ala Lys Gly Gly Ala Ser Gly Asp Trp Tyr Phe Asp Val Trp
 95                 100                 105                 110 ggc caa ggg acc acg gtc acc gtt tcc tct ggc ggt ggc ggt tct ggt      386
Gly Gln Gly Thr Thr Val Thr Val Ser Ser Gly Gly Gly Gly Ser Gly
                    115                 120                 125 ggc ggt ggc tcc ggc ggt ggc ggt tct gac atc cag ctg acc cag tct      434
Gly Gly Gly Ser Gly Gly Gly Gly Ser Asp Ile Gln Leu Thr Gln Ser
            130                 135                 140 cca tcc tca ctg tct gca tct ctg gga ggc gaa gtc acc atc act tgc      482
Pro Ser Ser Leu Ser Ala Ser Leu Gly Gly Glu Val Thr Ile Thr Cys
                145                 150                 155 aag gca agc caa gac att aag aag tat ata gct tgg tac caa cac aag      530
Lys Ala Ser Gln Asp Ile Lys Lys Tyr Ile Ala Trp Tyr Gln His Lys
160                 165                 170 cct gga aaa agt cct cgg cta ctc ata cac tac aca tct gta tta cag      578
Pro Gly Lys Ser Pro Arg Leu Leu Ile His Tyr Thr Ser Val Leu Gln
175                 180                 185                 190 cca ggc atc cca tcc agg ttc agt gga agt ggg tct ggg aga gat tat      626
Pro Gly Ile Pro Ser Arg Phe Ser Gly Ser Gly Ser Gly Arg Asp Tyr
                    195                 200                 205 tcc ttc agc atc cac aac ctg gag cct gaa gat att gca act tat tat      674
Ser Phe Ser Ile His Asn Leu Glu Pro Glu Asp Ile Ala Thr Tyr Tyr
            210                 215                 220 tgt cta cat tat gat tat ctg tac acg ttc gga ggg ggc acc aag ctg      722
Cys Leu His Tyr Asp Tyr Leu Tyr Thr Phe Gly Gly Gly Thr Lys Leu
                225                 230                 235 gag atc tagctgatca aagctctaga                                         748
Glu Ile
    240
```

<210> SEQ ID NO 4
<211> LENGTH: 240

<210> TYPE: PRT
<213> ORGANISM: Artificial Sequence
<220> FEATURE:
<223> OTHER INFORMATION: Description of Artificial Sequence: Synthetic chimeric amino acid sequence

<400> SEQUENCE: 4

```
Gln Val Gln Leu Gln Gln Ser Gly Ala Glu Leu Val Arg Pro Gly Thr
  1               5                  10                  15

Ser Val Lys Leu Ser Cys Lys Ala Ser Asp Tyr Thr Phe Thr Ser Tyr
             20                  25                  30

Trp Met Asn Trp Val Lys Gln Arg Pro Gly Gln Gly Leu Glu Trp Ile
         35                  40                  45

Gly Met Ile Asp Pro Ser Asp Ser Glu Thr Gln Tyr Asn Gln Met Phe
     50                  55                  60

Lys Asp Lys Ala Ala Leu Thr Val Asp Lys Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Lys Gly Gly Ala Ser Gly Asp Trp Tyr Phe Asp Val Trp Gly Gln
            100                 105                 110

Gly Thr Thr Val Thr Val Ser Ser Gly Gly Gly Ser Gly Gly Gly
            115                 120                 125

Gly Ser Gly Gly Gly Ser Asp Ile Gln Leu Thr Gln Ser Pro Ser
    130                 135                 140

Ser Leu Ser Ala Ser Leu Gly Gly Glu Val Thr Ile Thr Cys Lys Ala
145                 150                 155                 160

Ser Gln Asp Ile Lys Lys Tyr Ile Ala Trp Tyr Gln His Lys Pro Gly
                165                 170                 175

Lys Ser Pro Arg Leu Leu Ile His Tyr Thr Ser Val Leu Gln Pro Gly
            180                 185                 190

Ile Pro Ser Arg Phe Ser Gly Ser Gly Ser Gly Arg Asp Tyr Ser Phe
        195                 200                 205

Ser Ile His Asn Leu Glu Pro Glu Asp Ile Ala Thr Tyr Tyr Cys Leu
    210                 215                 220

His Tyr Asp Tyr Leu Tyr Thr Phe Gly Gly Gly Thr Lys Leu Glu Ile
225                 230                 235                 240
```

<210> SEQ ID NO 5
<211> LENGTH: 1479
<212> TYPE: DNA
<213> ORGANISM: Artificial Sequence
<220> FEATURE:
<223> OTHER INFORMATION: Description of Artificial Sequence: Synthetic chimeric nucleotide sequence
<220> FEATURE:
<221> NAME/KEY: CDS
<222> LOCATION: (40)..(1422)

<400> SEQUENCE: 5

```
gaattcggca cgagcttaag gcaccacttc ttagacatc atg gct tgg gtg tgg      54
                                            Met Ala Trp Val Trp
                                              1               5 acc ttg cta ttc ctg atg gca gct gcc aaa gtg ccc aag cag atc cag   102
Thr Leu Leu Phe Leu Met Ala Ala Ala Lys Val Pro Lys Gln Ile Gln
                 10                  15                  20 ttg gtg cag tct gga cct gag ctg aag aag cct gga gag aca gtc aag   150
Leu Val Gln Ser Gly Pro Glu Leu Lys Lys Pro Gly Glu Thr Val Lys
             25                  30                  35
```

```
atc tcc tgc aag gcc tct ggg tat cct ttc aca aac tat gga atg aac      198
Ile Ser Cys Lys Ala Ser Gly Tyr Pro Phe Thr Asn Tyr Gly Met Asn
         40                  45                  50 tgg gtg aag cag gct cca gga cag ggt tta aag tgg atg ggc tgg att      246
Trp Val Lys Gln Ala Pro Gly Gln Gly Leu Lys Trp Met Gly Trp Ile
 55                  60                  65 aac acc tcc act gga gag tca aca ttt gct gat gac ttc aag gga cgg      294
Asn Thr Ser Thr Gly Glu Ser Thr Phe Ala Asp Asp Phe Lys Gly Arg
 70                  75                  80                  85 ttt gac ttc tct ttg gaa acc tct gcc aac act gcc tat ttg cag atc      342
Phe Asp Phe Ser Leu Glu Thr Ser Ala Asn Thr Ala Tyr Leu Gln Ile
                 90                  95                 100 aac aac ctc aaa agt gaa gac atg gct aca tat ttc tgt gca aga tgg      390
Asn Asn Leu Lys Ser Glu Asp Met Ala Thr Tyr Phe Cys Ala Arg Trp
                105                 110                 115 gag gtt tac cac ggc tac gtt cct tac tgg ggc caa ggg acc acg gtc      438
Glu Val Tyr His Gly Tyr Val Pro Tyr Trp Gly Gln Gly Thr Thr Val
                120                 125                 130 acc gtt tcc tct ggc ggt ggc ggt tct ggt ggc ggt ggc tcc ggc ggt      486
Thr Val Ser Ser Gly Gly Gly Gly Ser Gly Gly Gly Gly Ser Gly Gly
         135                 140                 145 ggc ggt tct gac atc cag ctg acc cag tct cac aaa ttc ctg tcc act      534
Gly Gly Ser Asp Ile Gln Leu Thr Gln Ser His Lys Phe Leu Ser Thr
150                 155                 160                 165 tca gta gga gac agg gtc agc atc acc tgc aag gcc agt cag gat gtg      582
Ser Val Gly Asp Arg Val Ser Ile Thr Cys Lys Ala Ser Gln Asp Val
                170                 175                 180 tat aat gct gtt gcc tgg tat caa cag aaa cca gga caa tct cct aaa      630
Tyr Asn Ala Val Ala Trp Tyr Gln Gln Lys Pro Gly Gln Ser Pro Lys
                185                 190                 195 ctt ctg att tac tcg gca tcc tcc cgg tac act gga gtc cct tct cgc      678
Leu Leu Ile Tyr Ser Ala Ser Ser Arg Tyr Thr Gly Val Pro Ser Arg
                200                 205                 210 ttc act ggc agt ggc tct ggg ccg gat ttc act ttc acc atc agc agt      726
Phe Thr Gly Ser Gly Ser Gly Pro Asp Phe Thr Phe Thr Ile Ser Ser
         215                 220                 225 gtg cag gct gaa gac ctg gca gtt tat ttc tgt cag caa cat ttt cgt      774
Val Gln Ala Glu Asp Leu Ala Val Tyr Phe Cys Gln Gln His Phe Arg
230                 235                 240                 245 act cca ttc acg ttc ggc tcg ggg aca aaa ttg gag atc aaa gct cta      822
Thr Pro Phe Thr Phe Gly Ser Gly Thr Lys Leu Glu Ile Lys Ala Leu
                250                 255                 260 gag atc agc aac tcg gtg atg tac ttc agt tct gtc gtg cca gtc ctt      870
Glu Ile Ser Asn Ser Val Met Tyr Phe Ser Ser Val Val Pro Val Leu
                265                 270                 275 cag aaa gtg aac tct act act acc aag cca gtg ctg cga act ccc tca      918
Gln Lys Val Asn Ser Thr Thr Thr Lys Pro Val Leu Arg Thr Pro Ser
                280                 285                 290 cct gtg cac cct acc ggg aca tct cag ccc cag aga cca gaa gat tgt      966
Pro Val His Pro Thr Gly Thr Ser Gln Pro Gln Arg Pro Glu Asp Cys
         295                 300                 305 cgg ccc cgt ggc tca gtg aag ggg acc gga ttg gac ttt cta gag gat     1014
Arg Pro Arg Gly Ser Val Lys Gly Thr Gly Leu Asp Phe Leu Glu Asp
310                 315                 320                 325 ccc aaa ctc tgc tac ttg cta gat gga atc ctc ttc atc tac gga gtc     1062
Pro Lys Leu Cys Tyr Leu Leu Asp Gly Ile Leu Phe Ile Tyr Gly Val
                330                 335                 340 atc atc aca gcc ctg tac ctg aga gca aaa ttc agc agg agt gca gag     1110
Ile Ile Thr Ala Leu Tyr Leu Arg Ala Lys Phe Ser Arg Ser Ala Glu
         345                 350                 355
```

-continued

```
act gct gcc aac ctg cag gac ccc aac cag ctc tac aat gag ctc aat      1158
Thr Ala Ala Asn Leu Gln Asp Pro Asn Gln Leu Tyr Asn Glu Leu Asn
        360                 365                 370 cta ggg cga aga gag gaa tat gac gtc ttg gag aag aag cgg gct cgg      1206
Leu Gly Arg Arg Glu Glu Tyr Asp Val Leu Glu Lys Lys Arg Ala Arg
    375                 380                 385 gat cca gag atg gga ggc aaa cag cag agg agg agg aac ccc cag gaa      1254
Asp Pro Glu Met Gly Gly Lys Gln Gln Arg Arg Arg Asn Pro Gln Glu
390                 395                 400                 405 ggc gta tac aat gca ctg cag aaa gac aag atg gca gaa gcc tac agt      1302
Gly Val Tyr Asn Ala Leu Gln Lys Asp Lys Met Ala Glu Ala Tyr Ser
                410                 415                 420 gag atc ggc aca aaa ggc gag agg cgg aga ggc aag ggg cac gat ggc      1350
Glu Ile Gly Thr Lys Gly Glu Arg Arg Arg Gly Lys Gly His Asp Gly
            425                 430                 435 ctt tac cag ggt ctc agc act gcc acc aag gac acc tat gat gcc ctg      1398
Leu Tyr Gln Gly Leu Ser Thr Ala Thr Lys Asp Thr Tyr Asp Ala Leu
        440                 445                 450 cat atg cag acc ctg gcc cct cgc taacagccag ggcatttctc cctcacgggc     1452
His Met Gln Thr Leu Ala Pro Arg
    455                 460 agatccccgg gtaccgagct cgaattc                                        1479

<210> SEQ ID NO 6
<211> LENGTH: 461
<212> TYPE: PRT
<213> ORGANISM: Artificial Sequence
<220> FEATURE:
<223> OTHER INFORMATION: Description of Artificial Sequence: Synthetic
      chimeric amino acid sequence

<400> SEQUENCE: 6

Met Ala Trp Val Trp Thr Leu Leu Phe Leu Met Ala Ala Ala Lys Val
 1               5                  10                  15

Pro Lys Gln Ile Gln Leu Val Gln Ser Gly Pro Glu Leu Lys Lys Pro
            20                  25                  30

Gly Glu Thr Val Lys Ile Ser Cys Lys Ala Ser Gly Tyr Pro Phe Thr
        35                  40                  45

Asn Tyr Gly Met Asn Trp Val Lys Gln Ala Pro Gly Gln Gly Leu Lys
    50                  55                  60

Trp Met Gly Trp Ile Asn Thr Ser Thr Gly Glu Ser Thr Phe Ala Asp
65                  70                  75                  80

Asp Phe Lys Gly Arg Phe Asp Phe Ser Leu Glu Thr Ser Ala Asn Thr
                85                  90                  95

Ala Tyr Leu Gln Ile Asn Asn Leu Lys Ser Glu Asp Met Ala Thr Tyr
            100                 105                 110

Phe Cys Ala Arg Trp Glu Val Tyr His Gly Tyr Val Pro Tyr Trp Gly
        115                 120                 125

Gln Gly Thr Thr Val Thr Val Ser Gly Gly Gly Ser Gly Gly
    130                 135                 140

Gly Gly Ser Gly Gly Gly Gly Ser Asp Ile Gln Leu Thr Gln Ser His
145                 150                 155                 160

Lys Phe Leu Ser Thr Ser Val Gly Asp Arg Val Ser Ile Thr Cys Lys
                165                 170                 175

Ala Ser Gln Asp Val Tyr Asn Ala Val Ala Trp Tyr Gln Gln Lys Pro
            180                 185                 190

Gly Gln Ser Pro Lys Leu Leu Ile Tyr Ser Ala Ser Ser Arg Tyr Thr
```

-continued

```
                195                 200                 205
Gly Val Pro Ser Arg Phe Thr Gly Ser Gly Ser Gly Pro Asp Phe Thr
    210                 215                 220

Phe Thr Ile Ser Ser Val Gln Ala Glu Asp Leu Ala Val Tyr Phe Cys
225                 230                 235                 240

Gln Gln His Phe Arg Thr Pro Phe Thr Phe Gly Ser Gly Thr Lys Leu
                245                 250                 255

Glu Ile Lys Ala Leu Glu Ile Ser Asn Ser Val Met Tyr Phe Ser Ser
            260                 265                 270

Val Val Pro Val Leu Gln Lys Val Asn Ser Thr Thr Lys Pro Val
    275                 280                 285

Leu Arg Thr Pro Ser Pro Val His Pro Thr Gly Thr Ser Gln Pro Gln
    290                 295                 300

Arg Pro Glu Asp Cys Arg Pro Arg Gly Ser Val Lys Gly Thr Gly Leu
305                 310                 315                 320

Asp Phe Leu Glu Asp Pro Lys Leu Cys Tyr Leu Leu Asp Gly Ile Leu
                325                 330                 335

Phe Ile Tyr Gly Val Ile Ile Thr Ala Leu Tyr Leu Arg Ala Lys Phe
                340                 345                 350

Ser Arg Ser Ala Glu Thr Ala Ala Asn Leu Gln Asp Pro Asn Gln Leu
            355                 360                 365

Tyr Asn Glu Leu Asn Leu Gly Arg Arg Glu Glu Tyr Asp Val Leu Glu
            370                 375                 380

Lys Lys Arg Ala Arg Asp Pro Glu Met Gly Gly Lys Gln Gln Arg Arg
385                 390                 395                 400

Arg Asn Pro Gln Glu Gly Val Tyr Asn Ala Leu Gln Lys Asp Lys Met
                405                 410                 415

Ala Glu Ala Tyr Ser Glu Ile Gly Thr Lys Gly Glu Arg Arg Arg Gly
                420                 425                 430

Lys Gly His Asp Gly Leu Tyr Gln Gly Leu Ser Thr Ala Thr Lys Asp
            435                 440                 445

Thr Tyr Asp Ala Leu His Met Gln Thr Leu Ala Pro Arg
    450                 455                 460

<210> SEQ ID NO 7
<211> LENGTH: 443
<212> TYPE: PRT
<213> ORGANISM: Artificial Sequence
<220> FEATURE:
<223> OTHER INFORMATION: Description of Artificial Sequence: Synthetic
      chimeric amino acid sequence

<400> SEQUENCE: 7

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Pro Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Ser Thr Gly Glu Ser Thr Phe Ala Asp Asp Phe
    50                  55                  60

Lys Gly Arg Phe Asp Phe Ser Leu Glu Thr Ser Ala Asn Thr Ala Tyr
65                  70                  75                  80

Leu Gln Ile Asn Asn Leu Lys Ser Glu Asp Met Ala Thr Tyr Phe Cys
                85                  90                  95
```

-continued

```
Ala Arg Trp Glu Val Tyr His Gly Tyr Val Pro Tyr Trp Gly Gln Gly
         100                 105                 110
Thr Thr Val Thr Val Ser Ser Gly Gly Gly Ser Gly Gly Gly Gly
     115                 120                 125
Ser Gly Gly Gly Ser Asp Ile Gln Leu Thr Gln Ser His Lys Phe
130                 135                 140
Leu Ser Thr Ser Val Gly Asp Arg Val Ser Ile Thr Cys Lys Ala Ser
145                 150                 155                 160
Gln Asp Val Tyr Asn Ala Val Ala Trp Tyr Gln Gln Lys Pro Gly Gln
                 165                 170                 175
Ser Pro Lys Leu Leu Ile Tyr Ser Ala Ser Ser Arg Tyr Thr Gly Val
             180                 185                 190
Pro Ser Arg Phe Thr Gly Ser Gly Ser Gly Pro Asp Phe Thr Phe Thr
         195                 200                 205
Ile Ser Ser Val Gln Ala Glu Asp Leu Ala Val Tyr Phe Cys Gln Gln
210                 215                 220
His Phe Arg Thr Pro Phe Thr Phe Gly Ser Gly Thr Lys Leu Glu Ile
225                 230                 235                 240
Lys Ala Leu Glu Ile Ser Asn Ser Val Met Tyr Phe Ser Ser Val Val
                 245                 250                 255
Pro Val Leu Gln Lys Val Asn Ser Thr Thr Thr Lys Pro Val Leu Arg
             260                 265                 270
Thr Pro Ser Pro Val His Pro Thr Gly Thr Ser Gln Pro Gln Arg Pro
         275                 280                 285
Glu Asp Cys Arg Pro Arg Gly Ser Val Lys Gly Thr Gly Leu Asp Phe
290                 295                 300
Leu Glu Asp Pro Lys Leu Cys Tyr Leu Leu Asp Gly Ile Leu Phe Ile
305                 310                 315                 320
Tyr Gly Val Ile Ile Thr Ala Leu Tyr Leu Arg Ala Lys Phe Ser Arg
                 325                 330                 335
Ser Ala Glu Thr Ala Ala Asn Leu Gln Asp Pro Asn Gln Leu Tyr Asn
             340                 345                 350
Glu Leu Asn Leu Gly Arg Arg Glu Glu Tyr Asp Val Leu Glu Lys Lys
         355                 360                 365
Arg Ala Arg Asp Pro Glu Met Gly Gly Lys Gln Gln Arg Arg Arg Asn
370                 375                 380
Pro Gln Glu Gly Val Tyr Asn Ala Leu Gln Lys Asp Lys Met Ala Glu
385                 390                 395                 400
Ala Tyr Ser Glu Ile Gly Thr Lys Gly Glu Arg Arg Arg Gly Lys Gly
                 405                 410                 415
His Asp Gly Leu Tyr Gln Gly Leu Ser Thr Ala Thr Lys Asp Thr Tyr
             420                 425                 430
Asp Ala Leu His Met Gln Thr Leu Ala Pro Arg
         435                 440
```

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ctgaaagctt agatctgccc gtgagggaga aatgccctgg c                    41

```
<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcgatctaga aagtccaatc cggtcccctt cactg                          35

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gatctctaga ggatcccaaa ctctgctact tgc                            33

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcgatctaga gatcagcaac tcggtgatgt acttcag                        37

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 12

Gly Gly Gly Gly Ser Gly Gly Gly Gly Ser Gly Gly Gly Gly Ser
 1               5                  10                  15

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
agcttctaga gtttcagagc acagctctca cggcc                          35

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tcgatctaga gtctggttca cccctctgg                                 29
```

```
<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Ile Lys Ala Leu Glu Ile Ser Asn Ser
 1               5                  10

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Leu Asp Phe Leu Glu Asp Pro Lys Leu Cys Tyr Leu Leu Asp Gly
 1               5                  10                  15
```

What is claimed is:

1. A DNA encoding a bifunctional protein, wherein said protein comprises SEQ ID NO:7.

2. An in vitro or ex vivo host cell expressing the DNA claim 1.

3. A host cell according to claim 2 which is a cytotoxic lymphocyte (CTL).

4. An in vitro or ex vivo process for endowing a CTL with a defined, MHC-independent and MHC-unrestricted tumor cell specificity comprising introducing into said CTL the DNA of claim 1.

5. A method for the expression of a bifunctional protein comprising: culturing a host cell containing DNA encoding said protein under conditions which allow the expression of a protein encoded by the DNA of claim 1.

6. A composition-of-matter comprising a host cell according to claim 3.

7. A method of treating cancer, comprising contacting the cancer with CTL that expresses the DNA described in claim 1.

8. A vector comprising a DNA according to claim 1.

9. The DNA of claim 1, wherein said protein comprises the amino acid sequence as shown in SEQ ID NO:6.

10. The DNA of claim 9, comprising the nucleotide sequence as shown in SEQ ID NO:5.

* * * * *